United States Patent [19]

Bute

[11] 4,271,693

[45] Jun. 9, 1981

[54] DEVICE FOR TESTING SMOKE DETECTOR ALARMS

[76] Inventor: Donald R. Bute, 115 W. South Ave., Flora, Ill. 62839

[21] Appl. No.: 101,483

[22] Filed: Dec. 10, 1979

[51] Int. Cl.³ .................... G01M 19/00; G01N 37/00
[52] U.S. Cl. ............................... 73/1 G; 252/359 CG
[58] Field of Search ...................... 73/1 G; 116/214; 43/127, 128; 252/359 CG, 305

[56] References Cited

U.S. PATENT DOCUMENTS

| | | | |
|---|---|---|---|
| 1,225,798 | 5/1917 | Gaudy | 252/359 CG |
| 1,438,351 | 12/1922 | Ahern | 43/127 |
| 2,960,981 | 11/1960 | Robertson | 43/127 |
| 3,658,719 | 4/1972 | McConnaughey | 252/305 |
| 3,693,401 | 9/1972 | Purt | 73/1 G |
| 3,729,979 | 5/1973 | Wiberg | 73/1 G |

FOREIGN PATENT DOCUMENTS 52-43635 7/1977 Japan ........................ 73/1 G

*Primary Examiner*—S. Clement Swisher

*Attorney, Agent, or Firm*—Rogers, Eilers & Howell

[57] ABSTRACT

A device for testing smoke detector alarms comprises a base housing upon which is mounted an extendable telescopic assembly comprising three tubes, with the top tube having a combustible pellet mounted at its upper end. The pellet is composed of a substance that smolders upon heating rather than flaming or exploding. The housing contains electrical batteries wired in circuit with a heating element mounted adjacent the combustible pellet so that a switch can be operated to heat the heating element and cause the pellet to smolder so that smoke emerges from the pellet. The testing device can be placed in the extended position and the pellet held near a smoke detector and burned to ascertain whether the smoke detector alarm is functioning properly. After use the testing device can be placed in a compact storage position by sliding the extendable telescopic tubes so that they fit within each other.

If desired, the assembly upon which the pellet is mounted can comprise a unitary tubular section rather than a movable section.

6 Claims, 6 Drawing Figures

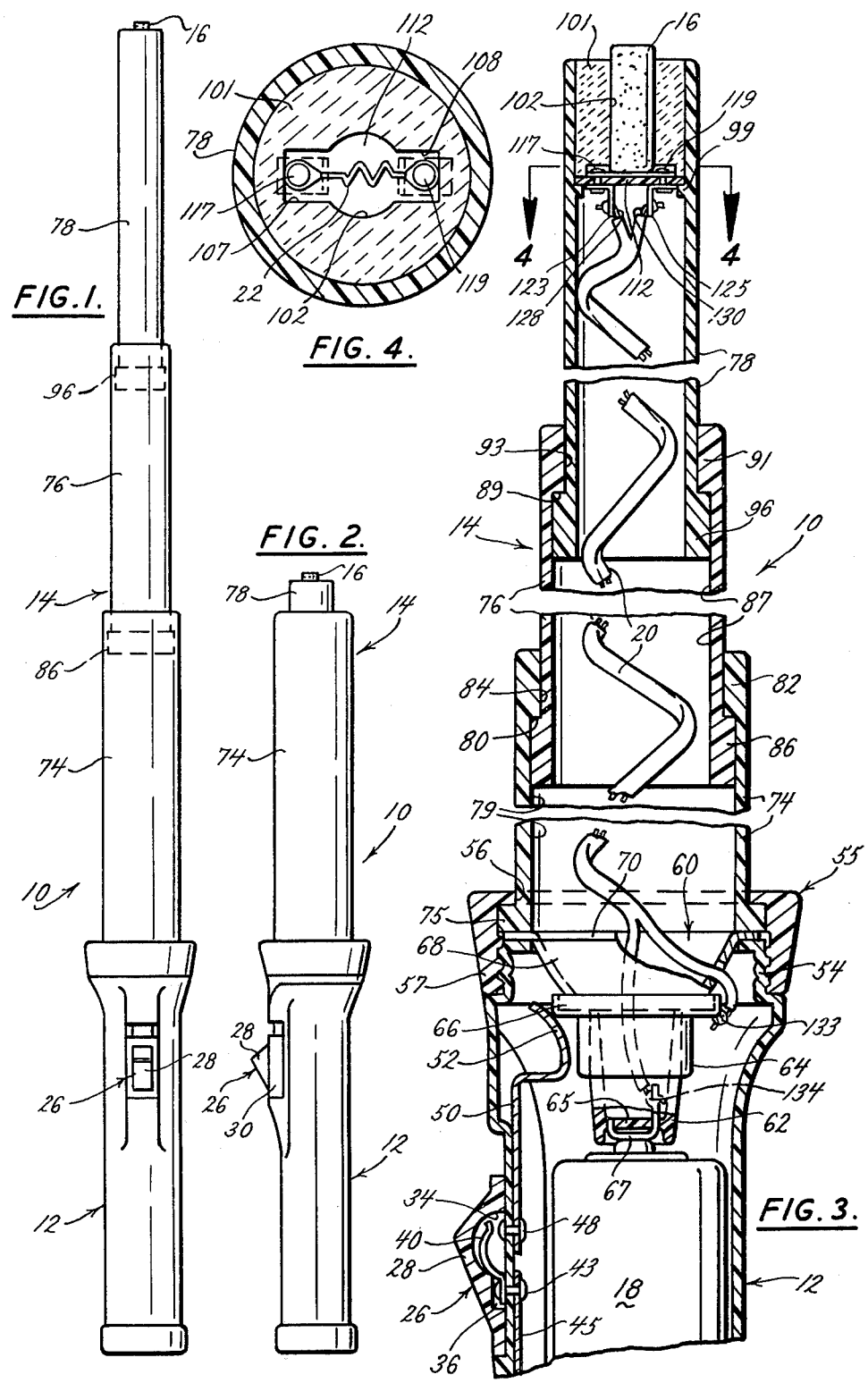

DEVICE FOR TESTING SMOKE DETECTOR ALARMS

BACKGROUND, FIELD AND SUMMARY OF THE INVENTION

The present invention is concerned with testing devices for smoke detectors and more particularly with a portable testing device.

In many homes, offices and other buildings throughout the United States there are in use smoke detectors for the purposes of sounding an alarm should a fire begin within the building. Generally, these smoke detectors have an electrical sensing circuit which is mounted within a ventilated housing to allow smoke to enter the housing and be sensed by the detector. When a sufficient amount of smoke is detected by the sensor, an alarm, such as a buzzer, is given so that people within the building are notified of the presence of a fire.

As a safety precaution, it is advisable to check these detectors to see that they are functioning properly. If they do not function properly, the smoke detector will not signal an alarm to give notice of a fire.

A common way of testing such smoke detectors is to light a match and place it near the detector so that smoke from the match will cause the alarm to sound. However, the lighting of the match creates a flame which is dangerous and can create a fire on the premises.

Furthermore, smoke detectors are frequently mounted on ceilings or other places in buildings so that they are not accessible for testing by a match or the like when the person is standing on a floor. As a result one has to stand on a stool, chair or table or other elevating means or the like to test the detector. Such a procedure creates a hazard of falling and personal injury.

The present invention improves over the prior art. The invention basically comprises a housing containing an electrical supply, such as batteries. Upon the upper end of the housing are mounted three telescopic tubes, the lower tube being firmly secured to the top of the housing, while the intermediate tube slides within the lower tube, and the upper tube slides within the intermediate tube. The upper tube has at its upper end a ceramic cylinder within which is mounted a combustible pellet. The lower end of the pellet is in contact with a heating element which is in electrical ciruit with the batteries. A switch on the housing operates to connect and disconnect the heating element from the batteries. The testing device can be placed in a storage position, in which the telescopic tubes are moved toward the housing to shorten the length of the device.

To use the device for testing smoke detectors, a pellet is placed within the ceramic cylinder, the second and third telescopic tubes are extended, and the housing is gripped by the operator's hand to hold the pellet well above the head of the operator so that the pellet is placed only a few inches from the smoke detector to be tested. When the pellet is in position, the housing switch is moved to complete the circuit through the heating element so that the pellet smolders to emit smoke. If the detector is operating properly, it will sound an alarm when the smoke enters the detector ventilation holes and is sensed by the detector sensing means.

After testing, the telescopic tubes are slid toward the housing to reduce the length of the testing device, and any charred remains of the pellet are removed by scraping or brushing of the ceramic cylinder. The testing device can then be placed in storage, and when further use is desired, another pellet can be inserted within the ceramic cylinder so that use can be repeated.

The use of the smoldering pellet avoids the use of a flaming tester, such as a flaming match. The pellet comprises a mixture of substances that smolder when heated by the heating element, rather than flaming or exploding as a result of the heat. The pellet can be comprised of any smoldering substance, but a mixture of fine sawdust mixed with vegetable oil, potassium chlorate, soap detergent, and a binder can be used as the smoldering substance. Mineral oil can be substituted for vegetable oil, or used in conjunction with vegetable oil if desired. These ingredients are compressed together and coated with a gelatin surface to form the pellet.

The extendable telescopic tubes allow the operator to place the smoldering pellet well above his or her head so that the need for standing upon a stool, chair or table or the like is avoided and testing may be done safely. The tester can also be used to reach smoke detectors which are mounted in positions where the operator must reach to one side or the other or downward to place the pellet next to the detector.

If desired the section upon which the pellet is mounted can be one singular tubular unit, rather than a sliding telescopic unit.

In a modification of the invention, a ceramic cup is used in place of the ceramic cylinder to hold the pellet.

It is an object of the invention to provide a means for testing smoke detectors of the type commonly used in homes and other buildings by providing a device that is easily collapsed and placed in a compact position for storage and yet is easily extended for ease of positioning a smoldering substance in proximity with a smoke detector so that smoke can be emitted to test the detector's alarm.

It is further an object of the invention to provide a safe means of testing smoke detector alarms without use of flames.

It is another object of the invention to provide a testing device for smoke detectors that reduces dependency of the operator upon using chairs, stools, ladders, and other means to position himself or herself near enough to a smoke detector to test the detector.

It is further an object to provide a compact portable testing device that can be handled easily and conveniently, and can be placed in permanent storage while consuming only a small amount of space.

DESCRIPTION OF THE DRAWINGS

FIG. 1 is a front plan view of the smoke detector testing device in the extended position;

FIG. 2 is a front plan view of the device in the compact storage position;

FIG. 3 is a diametrical section of the device of FIG. 1, with the telescopic tubes each shown broken, and with the lower section of the base not shown;

FIG. 4 is a section taken on the line 4—4 of FIG. 2 showing the heating element and the upper tube.

DESCRIPTION OF PREFERRED EMBODIMENT

Figure 5:
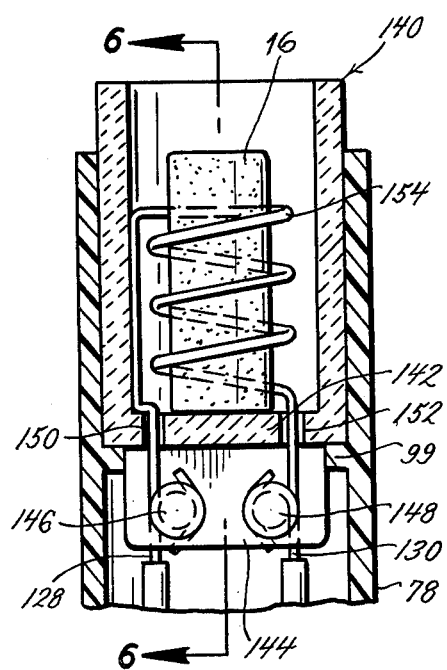
FIG. 5 is a diametrical section of a modification of the invention showing a cup for receiving the pellet.

Generally, the portable smoke detector testing device 10, as seen in the drawings, comprises a base housing 12, and extendable telescopic assembly 14 mounted above housing 12 with a combustable pellet 16 mounted at the tip of telescopic section 14. Three batteries, one such battery shown at 18, are mounted within the housing and supply electricity through wiring 20 to heat a heating element 22 to ignite and burn the pellet 16.

More specifically, the housing 12 is generally cylindrical in shape and can be the same shape as a standard flashlight housing. The bottom of the housing is closed so that three 1.5 volt batteries, such as shown at 18, may be housed within it, with the positive battery terminals of the bottom two batteries in electrical connection with the negative terminals of the top two batteries, as in a common flashlight circuit. The housing 12 has a standard flashlight battery type switch 26 which comprises a button 28 having two side flanges, one such flange being illustrated at 30 in FIG. 2. which fit around a rectangular section of the housing so that the button 28 may slide up and down relative to the housing. Referring to FIG. 3, the button has an inner concave cavity 34 which extends downwardly into a rectangular cavity 36. Mounted within the cavities 36 and 34 is a curved metal contact 40 having a straight flat portion fitting flush against the housing and being secured thereto by an electrical conducting rivet 43. The conducting rivet 43 secures a conducting metal strip 45 to the inside of the housing, the strip 45 extends downwardly into electrical contact with the bottom of the three batteries in the housing so that the strip 45 is in constant electrical contact with the three batteries 18 within the housing. Above rivet 43 a second conducting rivet 48 secures a conducting metal strip 50 against the inside of the housing. Strip 50 has a hook 52 which projects inwardly from the housing and thence curves upwardly to contact a conducting rim to be described. Movement of the button 28 upwardly from its position of FIG. 3 causes the lower curved portion of the cavity 34 to press the curved portion of contact 40 into contact with the exterior of rivet 48.

As seen in FIGS. 1 and 2, the peripheral portion of the housing beneath the switch tapers outwardly, and the rest of the peripheral portion of the housing tapers outwardly at a point above the switch 26. At the upper end of the housing 12 is a cylindrical threaded sleeve 54. A frustro conical cap 55 has an upper annular flange having an inner circular bore 56 and a lower annular portion 57 having an inner threaded bore which is screwed on to the housing sleeve 54. At the upper part of the housing 12 is a contact assembly 60 which comprises a lower plastic mount member 62 which fits within the bore of an intermediate cylindrical plastic sleeve 64 and is secured thereto as by adhesive or any sliding slot and notch type lock. Mount member 62 has a flat bottom side 65 having two slots which snugly receive the long and short vertical sections of a J shaped contact 67 which touches the positive terminal of the upper battery 18, as seen in FIG. 3. Intermediate sleeve 64 has a metallic electrically conducting rim 66 secured to its upper end, as by an adhesive or by a snap tab fit. Secured to the top of intermediate sleeve 64 is a plastic frustro conical section 68, which at its upper end has annular flange 70.

The housing 12, the switch 26, and the contact assembly 60 are parts commercially available as flashlight parts.

The extendable section 14 comprises three plastic cylindrical telescopic tubes comprising a lower tube 74, an intermediate tube 76, and an upper tube 78. The tubes are shown in the extended position in FIGS. 1 and 3 and in the compact or storage position in FIG. 2. Referring to FIG. 3, the lower tube 74 has at its lower end an outwardly projecting annular flange 75. The tube 74 snugly extends through the bore 56 of cap 57 to allow the tube flange 75 to fit beneath the inner shoulder of the upper cap flange so that when the cap 57 is threaded upon housing sleeve 54 the tube flange 75, and thus tube 74, is held securely against the housing 12. The inside of tube 74 has extending from its bottom a cylindrical bore 78 which extends upwardly to an annular shoulder 80 formed by an inwardly projecting cylindrical lug 82 at the top of tube 74. The cylindrical lug 82 has a cylindrical bore 84.

The intermediate telescopic tube 76 at its lower end has an enlarged annular flange 86 which is snugly telescopically received within the larger bore 79 of lower tube 74 to telescopically slide therein so that the upper edge of the flange 86 abuts the shoulder 80 of lug 82 when the intermediate tube 76 is extended upwardly to its limit, as shown in FIG. 3. The outer surface of tube 76 is telescopically received within the bore 84 of lug 82 so that it can slide therein. The tube 76 has an inner cylindrical bore 87 which extends upwardly into a circular shoulder 89 formed at the lower end of an inwardly projecting cylindrical lug 91. The lug 91 has an inner cylindrical bore 93.

The upper tube 78 at its lower end has an outwardly projecting annular flange 96 which is telescopically received within the bore 87 of tube 76 to snugly slide therein. Tube 78 has a cylindrical interior bore which extends upwardly to an annular inwardly projecting rim 99. Above rim 99, the inner cylindrical bore of tube 78 continues and telescopically receives with a snug fit a ceramic cylinder 101 having a cylindrical exterior surface and a cylindrical inner bore 102 which snugly telescopically receives the pellet 16 at the upper end of tube 78.

The pellet 16 is of a generally cylindrical shape, and contains a compressed mixture of fine sawdust mixed with a vegetable oil, potassium chlorate, iron oxide, soap detergent, and a binder. The soap detergent can be common laundry detergent. These ingredients are compressed together, and if desired can be coated with a gelatin surface. The pellet is designed to smolder rather than flame, so that smoke will be given off by slow combustion. Generally, any combustible substance that is not of an explosive or flammable nature can be used for the ingredients of the pellet 16. Mineral oil can be substituted for vegetable oil or used in conjunction with vegetable oil, if desired.

The ceramic cylinder 101, at its lower end, has two rectangular notches 107 and 108, as seen in FIG. 4. Notches 107 and 108 extend only a slight distance upwardly from the bottom of the cylinder 101, and extend outwardly from bore 102. As seen in FIG. 3 and 4, a rigid circular plastic disc 112 has its outer underside resting upon rim 99, and its outer edge flush against the interior bore surface of tube 78 to be supported within tube 78 so that the cylinder 101 can rest upon it. The disc 112 can be secured to rim 99 by an adhesive, and if desired, the bottom of cylinder 101 can also be secured to plate 112 as by an adhesive.

The heating element 22, which is of metal, extends across the top of disc 112 so that it is in contact with the lower surface of the pellet 16. Rivets 117 and 119 secure the ends of heating element 22 to the disc 112 and also secure angle contacts 123 and 125 to the disc bottom.

The wiring 20 provides electrical connection between the heating element 22 and the contact assembly 60, and comprises two insulated wires 128 and 130 which are secured as by soldering to the angle contacts 123 and 125, respectively, and thence extend downwardly with wire 128 soldered at 133 to the rim 66, and the wire 130 soldered to the J contact 67 at 134.

Figure 6:
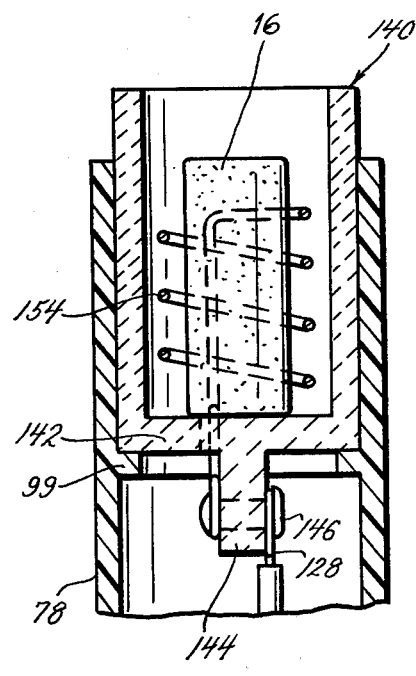
FIG. 6 is a section taken on the line 6—6 of FIG. 5 showing the modification.

FIGS. 5 and 6 show a modification of the invention, in which a cylindrical ceramic cup 140, having a cylindrical outer wall and a bottom wall 142 is snugly received within the upper end of upper tube 78 to rest upon the annular rim 99 so that the cup is firmly fitted within tube 78. Extending downwardly from cup wall 142, through the interior of rim 99, is a tab 144 having rivet contacts 146 and 148 to which the wires 128 and 130 are connected. The cup bottom wall 142 has a pair of cylindrical bores 150 and 152. A spiral heating coil 154 fits within the cup 140 and has its terminal ends extending through the bores 150 and 152 so that they are both connected to the contacts 146 and 148 to complete a circuit through the wires 128 and 130. The coil 154 spirals around the pellet 16 so that when the coil is energized and heated the pellet will be ignited to smolder.

Operation

In operation, the testing device 10 can be maintained in the compact storage position of FIG. 3 until its use is desired. Upon being removed from storage, the device 10 can be carried by hand to a position in a house or building where a smoke detector is located. Generally, such smoke detectors are battery operated and have a housing with vents to allow entry of smoke so that the smoke can be detected by a smoke sensing means within the housing. For present purposes, it will be assumed that the smoke detector is mounted upon the ceiling in the hallway of a house about ten feet above the floor.

The device 10 is carried by the operator to a position beneath the smoke detector. The pellet 16 is then placed within the ceramic cylinder 101 as shown in FIG. 3. The two tubes 76 and 78 are then moved to the extended positions shown in FIG. 1 by first grasping tube 78 and pulling it away from tubes 76 and 74 until annular flange 96 abuts the circular shoulder 89. The snugness of the fit of flange 96 within bore 87 holds tube 78 in the extended position. Tube 76 is then grasped and pulled away from tube 74 until the flange 86 abuts the shoulder 80 of lug 82 as shown in FIG. 3. The fittings of the flanges 86 and 96 within bores 79 and 87 respectively are snug enough so that tubes 76 and 74 maintain the position of FIGS. 1 and 3 and do not slide downward without additional force being exerted against them.

If desired, the annular flanges 86 and 96 of tubes 76 and 78 respectively can be provided with peripheral grooves and the inner walls of tubes 74 and 76 can be provided with knobs to lock with those grooves to also hold the tubes in the extended position.

In the extended position of FIG. 1, the operator's hands can grasp the housing 12 and lift it upward to likewise move the extendable section 14 upward so that the pellet 16 is moved to within two to three inches of the smoke detector vents. Switch 26 can then be operated by moving the button 28 upward to move curved metal contact 40 into contact with rivet 48. When this occurs, the electrical circuit is completed through strip 50, rim 66, the electrical wiring 20, contacts 123 and 125, heating element 22, J contact 134, the batteries 18, and strip 45 so that the heating element 22 is heated. The pellet 16, being mounted so that its lower end is in contact with heating element 22, begins smoldering as a result of the heat from element 22, so that smoke from the pellet 16 flows to the sensing means in the smoke detector. The heat provided by the heating element is not great enough to cause an explosion or flaming. If the smoke detector is operating properly, it will give an alarm of some nature, such as a buzzing sound, as is known in the art. If the detector does not give the appropriate alarm, then the operator can then take steps to check the detector for defects, such as weak batteries.

After the pellet 16 smolders to the extent desired, button 28 can be moved downward to disengage contact 40 from rivet 48 to break the circuit. Tube 76 can then be grasped by the hand and slid downwardly until the top of the tube is about flush with the top of tube 74. The upper tube 78 can then be slid downward to the position shown in FIG. 2 and at this point, a scraping device such as a knife or file or the like can be used to remove any charred portions remaining of pellet 16 from the ceramic cylinder 101. After inspecting to be sure that no remaining portions of the pellet are still burning, the testing device 10 can again be returned to storage. For safety in storage, it is best to remove the batteries from the housing by unscrewing cap 55 and removing the batteries through the top of the housing.

The modification of FIGS. 5 and 6 functions in the same manner as previously described. However, in this modification the heating coil 154 does not grip pellet 16 so that the cup 140 should not be tilted to allow the pellet to slide out of the cup.

The testing device 10 thus eliminates the need for using matches or other flammable substances to test a smoke detector. It also allows a smoke detector testing without standing upon a ladder, chair or the like and thus eliminates danger from falling.

The extendable section 14 has been described as having three telescopic tubes, which is preferred. However, if desired a pair of telescopic tubes can be used, although in such a situation the length of the extendable section in the compact position will be longer than with three tubes if the overall length of the extendable section in the extended position remains the same. Likewise, four or more telescopic tubes can be used in which case the length of the extendable section in the compact position will be shorter than with three tubes, when the same length of the extendable section in the extended position is desired. The length of the telescopic tubes can be modified to make the length of extendable section 14 as long or as short as desired.

If desired, the tubular sections 74, 76, 78 can be molded to be unitary in the extended position of FIGS. 1 and 3 so that the assembly does not slide telescopically but remains of a fixed length. This fixed length can be whatever length is desired. Furthermore, a single tube such as tube 74 can be used with the ceramic cylinder or the ceramic cup mounted in its end. The unitary tube arrangement is preferable when the smoke alarm is not hard to reach.

What is claimed is:
1. A device for testing smoke detector alarms comprising:
   (a) a housing;
   (b) an extendable section mounted upon the housing extendable into a long position and to a short position or shorter length than the long position;

(c) a combustible member mounted on the extendable section for creating smoke by smoldering;
(d) means for applying heat to the combustible member to cause it to smolder, comprising an electrical heating element.

2. The structure of claim 1 wherein the extendable section comprises a first tube telescopically mounted to a second tube.

3. The structure of claim 1 wherein the extendable section comprises a plurality of telescopic tubes including an upper telescopic tube, with the combustible member mounted at the outer end of the outer tube.

4. The structure of claim 4 wherein the combustible member comprises sawdust, vegetable oil, potassium chlorate, and iron oxide.

5. The structure of claim 1 wherein the means for applying heat further comprises batteries electrically connected to the heating element, and a switch positionable to disconnect and connect the heating element with the batteries.

6. A device for testing smoke detector alarms comprising:
(a) a housing;
(b) a section mounted on the housing;
(c) a combustible member mounted on the end of the section for creating smoke by smoldering; and
(d) means for applying heat to the combustible member to cause it to smolder, comprising an electrical heating element.

* * * * *

UNITED STATES PATENT OFFICE
CERTIFICATE OF CORRECTION

Patent No. 4,271,693     Dated June 9, 1981

Inventor(s)     BUTE, DONALD R.

It is certified that error appears in the above-identified patent and that said Letters Patent are hereby corrected as shown below:

Column 6, line 68, change "or" to --of--;

Column 7, line 13, change "Claim 4" to --Claim 1--.

Signed and Sealed this

Sixth Day of October 1981

[SEAL]

Attest:

GERALD J. MOSSINGHOFF

*Attesting Officer*     *Commissioner of Patents and Trademarks*